United States Patent
Griffiths-Brophy et al.

(10) Patent No.: US 9,895,305 B2
(45) Date of Patent: Feb. 20, 2018

(54) SKIN CLEANSING COMPOSITIONS COMPRISING BIODEGRADABLE ABRASIVE PARTICLES

(71) Applicant: The Procter & Gamble Company, Cincinnati, OH (US)

(72) Inventors: Susan Adair Griffiths-Brophy, Middletown, OH (US); Chu Zhu, West Chester, OH (US); Robert Bao Kim Ha, Liberty Township, OH (US); Timothy Alan Fornshell, Oregonia, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/824,357

(22) Filed: Aug. 12, 2015

(65) Prior Publication Data
US 2017/0042786 A1 Feb. 16, 2017

(51) Int. Cl.
| A61Q 19/10 | (2006.01) |
| --- | --- |
| A61K 8/85 | (2006.01) |
| A61Q 15/00 | (2006.01) |
| A61Q 19/02 | (2006.01) |
| A61K 8/29 | (2006.01) |
| A61Q 19/00 | (2006.01) |
| A61K 8/02 | (2006.01) |
| A61Q 19/04 | (2006.01) |

(52) U.S. Cl.
CPC .............. *A61K 8/85* (2013.01); *A61K 8/0241* (2013.01); *A61K 8/29* (2013.01); *A61Q 15/00* (2013.01); *A61Q 19/007* (2013.01); *A61Q 19/02* (2013.01); *A61Q 19/04* (2013.01); *A61Q 19/10* (2013.01); *A61K 2800/28* (2013.01); *A61K 2800/412* (2013.01); *A61K 2800/654* (2013.01)

(58) Field of Classification Search
CPC .......... A61Q 11/00; A61Q 19/10; A61Q 5/02; A61Q 19/00; A61Q 1/12; A61K 2800/28; A61K 2800/412; A61K 2800/654; A61K 8/85; A61K 8/0245; A61K 8/025; A61K 8/04; A61K 8/046; A61K 8/19; A61K 8/87
See application file for complete search history.

(56) References Cited

U.S. PATENT DOCUMENTS

| 6,699,963 | B2 | 3/2004 | Noda et al. |
| --- | --- | --- | --- |
| 8,440,602 | B2 | 5/2013 | Gonzales et al. |
| 8,440,603 | B2 | 5/2013 | Gonzales et al. |
| 8,470,759 | B2 | 6/2013 | Gonzales et al. |
| 8,546,316 | B2 | 10/2013 | Perez-Prat Vinuesa et al. |
| 8,629,095 | B2 | 1/2014 | Deleersnyder et al. |
| 8,680,036 | B2 | 3/2014 | Gonzales et al. |
| 8,703,685 | B2 | 4/2014 | Gonzales et al. |
| 8,759,270 | B2 | 6/2014 | Perez-Prat Vinuesa et al. |
| 8,852,643 | B2 | 10/2014 | Gonzales et al. |
| 8,968,787 | B2 | 3/2015 | Gittleman |
| 9,163,201 | B2 | 10/2015 | Gonzales et al. |
| 2009/0269288 | A1* | 10/2009 | Lavrova .................. A61K 8/19 424/56 |
| 2011/0150787 | A1 | 6/2011 | Gonzales et al. |
| 2011/0150788 | A1 | 6/2011 | Gonzales et al. |
| 2011/0150951 | A1 | 6/2011 | Gonzales et al. |
| 2011/0262504 | A1 | 10/2011 | Deleersnyder et al. |
| 2012/0071379 | A1 | 3/2012 | Gonzales et al. |
| 2012/0071380 | A1 | 3/2012 | Gonzales et al. |
| 2012/0321567 | A1 | 12/2012 | Gonzales et al. |
| 2012/0321568 | A1 | 12/2012 | Gonzales et al. |
| 2012/0321680 | A1* | 12/2012 | Gonzales .......... C11D 17/0013 424/401 |
| 2013/0022556 | A1 | 1/2013 | Gonzales et al. |
| 2013/0039961 | A1 | 2/2013 | Gonzales et al. |
| 2014/0026916 | A1* | 1/2014 | Havens ..................... A61K 8/85 132/200 |
| 2014/0352721 | A1 | 12/2014 | Gonzales et al. |
| 2014/0352722 | A1 | 12/2014 | Gonzales et al. |
| 2014/0357544 | A1 | 12/2014 | Gonzales et al. |
| 2015/0007399 | A1* | 1/2015 | Gonzales ................. A61K 8/25 15/104.93 |
| 2015/0007400 | A1 | 1/2015 | Gonzales et al. |

FOREIGN PATENT DOCUMENTS

| EP | 0 739 368 B1 | 2/2003 |
| --- | --- | --- |
| EP | 2 338 962 A1 | 6/2011 |
| JP | 04-331294 A | 11/1992 |
| JP | 2008-37841 A | 2/2008 |
| JP | 2010-270085 A | 12/2010 |

OTHER PUBLICATIONS

U.S. Appl. No. 14/624,477, filed Feb. 17, 2015, Denis Alfred Gonzales et al.

* cited by examiner

*Primary Examiner* — Audrea Buckley
(74) *Attorney, Agent, or Firm* — Betty J. Zea (57) ABSTRACT

A skin cleansing composition is provided. The skin cleansing composition comprises from about 0.1% to about 15%, by weight, of a plurality of biodegradable abrasive particles. The biodegradable abrasive particles comprise a safe and effective amount of polyhydroxy alkanoate (PHA) biodegradable polymeric material and comprise a particle size range from 10 μm to 1500 μm. The composition also comprises a multimodal particle size distribution of the biodegradable abrasive particles. The composition further comprises a dermatologically acceptable carrier.

25 Claims, 6 Drawing Sheets

SKIN CLEANSING COMPOSITIONS COMPRISING BIODEGRADABLE ABRASIVE PARTICLES

FIELD OF THE INVENTION

The present invention relates to skin care or skin cleansing compositions comprising biodegradable abrasive particles, and methods of making and using the same.

BACKGROUND OF THE INVENTION

Skin cleansing compositions routinely include abrasive particles for cleansing the skin (e.g., removal of dirt, sebum, or oil) or improving the appearance of the skin (e.g., exfoliation). Abrasive particles are commonly made from petroleum-based synthetic polymers like polystyrene, cross-linked styrene (XST), polyurethane (PU), polyolefins or waxes. Unfortunately, these petroleum-based synthetic polymers may present long-term disposal problems and potentially have adverse effects on the environment.

On the other hand, natural abrasives such as abrasives derived from plants, shells such as from nuts, or mineral materials, may present poor aesthetics. They may also be too abrasive for use on facial skin. Thus some abrasive particles for use in a skin cleansing composition tend to be overly abrasive and can damage the skin, especially when applied on more sensitive facial skin surfaces.

Recently, biobased polymers like polyhydroxy alkonates (PHA) have attracted significant attention because they are made from renewable plant resources. These materials can be recycled using biological processes (i.e., biorenewable or biodegradable) to reduce greenhouse gas emission and conserve resources.

Features such as size, texture and shape of the abrasive particles also play an important role in the consumer acceptance of skin cleansing compositions. In many cases the visibility of larger abrasive particles signals exfoliation benefits of the product to consumers. Larger abrasive particles also tend to have better tactile properties in use. Visible particles also distinguish particular products in the market place and to identify products having particular beneficial cleaning properties via abrasive particles. Larger sized particles however, that are more visable, tend to be less abrasive and may yield poor or inadequate cleansing and exfoliation performance as evidenced by lack of removal of skin cells, soil or make-up, which may remain on the skin after use.

Furthermore, cleansing compositions with smaller particles may feel more gritty or may be overly abrasive. Consumers selecting a facial cleanser may avoid compositions that feel gritty or overly coarse. Thus formulators often must balance between smaller particles which may be overly abrasive and coarse potentially causing damage on the skin surface, and larger, gentler abrasive particles with a better tactile feel and that are more visable in the product but with reduced or inadequate exfoliation efficacy.

Therefore, improved skin cleansing compositions that comprise biodegradable abrasive particles with adequate skin cleansing and exfoliating benefits and good tactile properties are needed. Providing a skin cleansing composition with the right balance of these particle properties provides multiple consumer benefits. These improved compositions are more biodegradable, have visible larger particles that have desired tactile properties and have adequate exfoliation efficacy from a distribution of smaller particles with larger surface area.

SUMMARY OF THE INVENTION

The present invention is directed to a skin cleansing composition comprising biodegradable abrasive particles. The skin cleansing composition comprises:

from about 0.1% to about 15%, by weight of the composition, of a plurality of biodegradable abrasive particles comprising a safe and effective amount, by weight of the particles, of polyhydroxy alkanoate (PHA) biodegradable polymeric material and a particle size range from about 10 µm to 1500 µm;

a multimodal particle size distribution of the biodegradable abrasive particles; and a dermatologically acceptable carrier.

In one embodiment the multimodal particle size distribution comprises distribution A and distribution B, in another embodiment the multimodal particle size distribution comprises distribution A, distribution B and distribution C. Preferably distribution A comprises from about 55% to about 90% by weight of the abrasive particles and distribution B comprises from about 10% to about 45% by weight of the abrasive particles. Distribution A may comprise a particle size range from about 10 µm to 300 µm and distribution B may comprise a particle size range from 300 µm to about 1500 µm.

In another embodiment distribution A may comprise a particle size range from about 10 µm to about 300 µm and distribution B may comprise a particle size range from about 600 µm to about 1500 µm, and in a further embodiment distribution A comprises a particle size range from about 10 µm to 300 µm, distribution B comprises a particle size range from 300 µm to about 600 µm and distribution C comprises a particle size range from about 600 µm to about 1500 µm.

Preferably distribution A and distribution B have a ratio of abrasive particle from 0.9:0.1 to 0.1:0.9, of A to B.

In another aspect, the present invention relates to a method for cleansing a human's skin surface comprising topically contacting the skin surface with a skin cleansing composition herein, and additionally followed by a rinsing step.

It is an advantage of the compositions according to the present invention that they may be used to cleanse facial skin surfaces, while providing a good surface safety profile. A further advantage of the present invention is that the abrasive particles can be formulated at very low levels, while still providing the above benefits. In another aspect, the present invention relates to use of biodegradable abrasive particles in a skin cleansing composition, for delivering a benefit selected from the group consisting of mild skin exfoliation, dirt removal from a skin surface, abrasive particle biodegradability; more visible larger particles that have consumer desired tactile properties; colored particles that can provide coloring to a translucent or transparent cosmetic composition base, and combinations thereof. These and other aspects of the present invention will become more apparent upon reading the following detailed description of the invention.

DETAILED DESCRIPTION OF THE INVENTION

The patent or application file contains at least one photograph executed in color. Copies of this patent or patent application publication with color photographs will be provided by the Office upon request and payment of the necessary fee.

Except as otherwise noted, the articles "a", "an", and "the" mean "one or more."

The term "comprising" means that other steps and other ingredients which do not affect the end result can be added, and this term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein. Particularly, the compositions of the present invention contain biodegradable abrasive particles, and one or more additional or optional ingredients as described hereinafter.

All percentages, parts and ratios are based upon the total weight of the compositions of the present invention, unless otherwise specified. All such weights as they pertain to listed ingredients are based on the active level and, therefore do not include carriers or by-products that may be included in commercially available materials. The components, including those which may optionally be added, as well as methods for preparation, and methods for use, are described in detail below.

All ratios are weight ratios unless specifically stated otherwise. All temperatures are in Celsius degrees (° C.), unless specifically stated otherwise.

As used herein "biodegradable" means chemical dissolution of the organic material by bacteria or other biological means at a certain rate (%) or above according to the Biodegradability Test as described in the Method Section herein.

As used herein "derivatives" means an ester, ether, amide, hydroxyl, and/or salt structural analogue of the relevant compound.

As used herein "dermatologically acceptable" means that the compositions or components described are suitable for use in contact with human skin tissue, preferably facial skin surfaces, without undue toxicity, incompatibility, instability, allergic response, discomfort, and the like.

As used herein "exfoliation" or "mild skin exfoliation" means removal of dead skin cells from the outermost layer of the skin whilst minimizing the risk of over-exfoliating the skin, which may otherwise result in damaged and/or redness to the skin, or discomfort to the user.

As used herein "surface safety profile" means that the compositions or components thereof are not overly abrasive to human skin tissue, particularly human facial skin tissue, so as to not significantly scratch or damage the surface (e.g., redness) while still providing a good cleaning performance on the skin surface.

As used herein "homogeneous mixture" of the colorant and the biodegradable polymeric material means that the abrasive particles are formed by mixing the colorant and the biodegradable polymeric material so that the colorant is not just applied to the surface of the biodegradable polymeric material and/or the abrasive particle, but the colorant is distributed, to some extent, throughout the biodegradable polymeric material forming the particle. "Homogeneous mixture" also includes the uniform mixture of the colorant and the biodegradable polymeric material forming the particle wherein the colorant is uniformly distributed throughout the biodegradable polymeric material of the particle.

Skin Cleansing Compositions

The present invention is directed to a skin cleansing composition comprising: biodegradable abrasive particles present at a level of from about 0.1 wt % to about 15 wt %, in another embodiment from about 0.3 wt % to about 8 wt %, in another embodiment from about 0.5 wt % to about 5 wt %, or in another embodiment from about 1 wt % to about 3 wt %, and a dermatologically acceptable carrier.

The skin cleansing compositions according to the present invention are designed as skin cleansers for a variety of human skin surfaces. Examples of the skin cleansing compositions include, a facial cleanser, a body wash, a hand cleanser, or a body cleanser. In an embodiment, the skin cleansing compositions herein are suitable for use as a facial cleanser.

The skin cleansing compositions may have a viscosity in the range of from about 100 cps to about 1,000,000 cps, preferably from about 1,000 cps to about 300,000 cps, or more preferably from about 5,000 cps to about 200,000 cps. The viscosity is measured at 20 sec$^{-1}$ and 20° C. with a Rheometer, model AR 1000 (Supplied by TA Instruments) with a 4 cm conic spindle in stainless steel, 2° angle (linear increment from 0.1 to 100 sec$^{-1}$ in max. 8 minutes).

Biodegradable Abrasive Particles

In an embodiment a skin cleansing composition is provided comprising:

from about 0.1% to about 15%, by weight of the composition, of a plurality of biodegradable abrasive particles comprising a safe and effective amount, by weight of the particles, of polyhydroxy alkanoate (PHA) biodegradable polymeric material and a particle size range from about 10 μm to 1500 μm;

a multimodal particle size distribution of the biodegradable abrasive particles; and a dermatologically acceptable carrier.

The applicants have surprisingly found that biodegradable abrasive particles according to the present invention, when formulated into the skin cleansing compositions, provide good cleansing performance on human skin surfaces, while providing a good surface safety profile. By controlling the particle size distribution and providing a multimodal distribution of the biodegradable abrasive particles, multiple benefits are obtained. These benefits include: biodegradability, enhanced visibility to the consumer of the larger particles to signal benefits, better tactile properties, good exfoliation due to larger surface area and irregular shape of the smaller particles, no or minimal bleeding or migration of color from the abrasive particles into the cleansing composition, and the use of abrasive particles to color translucent, transparent, and/or white cosmetic composition.

In an embodiment, the biodegradable abrasive particles have an acceptable surface safety profile and thus are not overly abrasive on contact with skin. In another embodiment, the biodegradable abrasive particles are dermatologically acceptable.

In an embodiment, the abrasive particles according to the present invention are considered biodegradable. Biodegradation is the chemical dissolution of materials by bacteria or other biological means. Currently, biodegradability is commonly associated with environmentally friendly products that are capable of decomposing back into natural elements. Organic material can be degraded aerobically with oxygen, or anaerobically without oxygen. Readily biodegradable materials discussed herein are materials which also may biodegrade according to protocol and requirement described in the Biodegradability Test as disclosed in the Method Section here. This Biodegradability Rate would include all components except for inorganic materials and water.

In one embodiment, the biodegradable abrasive particles herein have a Biodegradable Rate of about 60% to about 100%, or about 80% to about 100%, or about 85% to about 100%, at least about 60%, or at least about 70%, or at least about 80%, or at least 90%, as determined after either 28 days or after 90 days according to the Biodegradability Test as disclosed herein. In another embodiment herein, the Biodegradable Rate of the abrasive particles is at most about 100%, 99%, 95%, 90%, 85% or 80% as determined after either 28 days or after 90 days according to the Biodegradability Test as disclosed herein.

In an embodiment, the biodegradable abrasive particles comprise one or more polymers of the class of polyhydroxy alkanoates (PHA). In an embodiment the PHA may be selected from the group consisting of poly-3-hydroxybutyrate (PHB), poly-3-hydroxyhexanoate, poly-3-hydroxyvalerate, poly-3-hydroxy-butyrate-co-3-hydroxyvalerate (PHBV), poly-3-hydroxybutyrate-co-3-hydroxyhexanoate (PHBH), and blends thereof.

In an embodiment, the biodegradable abrasive particles of the present invention are poly-3-hydroxybutyrate-co-3-hydroxyvalerate (PHBV). PHBV polymers are biopolymers that are synthesized by bacteria as intracellular carbon and energy storage granules under limited nutrients in the presence of excess carbon source. The molecular weight of these polymers varies and may be from 200 KDa to 3,000 KDa depending on the microorganism, nutrients and growth conditions. The molecular weight of PHBV polymers ranges from 1,000 g/mol to 3,000,000 g/mol, preferably from 20,000 g/mol to 700,000 g/mol, more preferably from 100,000 g/mol to 500,000 g/mol.

The skin cleansing composition herein may include additional, optional biodegradable abrasive particles that are selected from the group of polymeric material consisting of:

(a) one or more homo-polymers or co-polymers selected from the group consisting of polylactic acid derivatives (PLA), polycaprolactone (PLC), poly(glycolic acid) (PGA), and blends thereof;

(b) aliphatic and/or, aromatic co-polyesters, preferably wherein said co-polyester is selected from co-polyester containing succinic, adipic, terepthalic diacids, propanediol, butanediol, pentanediol monomer or blends thereof, preferably polybutylene succinate (PBS), or polybutylene-adipate-terephtalate (PBAT);

(c) starch, thermoplastic starch (TPS), or blends thereof;

(d) thermoplastic cellulose (TPC) derivative selected from the group consisting of cellulose ester, cellulose ether, cellulose alkanoate and blends thereof, preferably said thermoplastic cellulose is cellulose acetate, nitrocellulose or blends thereof; and (e) combinations of (a) to (d).

In an embodiment the biodegradable abrasive particles have a multimodal particle size distribution. The biodegradable abrasive particles may comprise at least distribution A and a second distribution (e.g. distribution B and/or C), wherein distribution A may comprise a particle size range from 10 μm to 300 μm or 50 μm to 300 μm. In another embodiment the multimodal particle size distribution of the biodegradable abrasive particles comprises at least distribution A and distribution B wherein distribution A may comprise a particle size range from 10 μm to 300 μm and distribution B may comprise a particle size range from 300 μm to 1500 μm.

In another embodiment the multimodal distribution of the biodegradable abrasive particles comprise at least distribution A (wherein distribution A may comprise a particle size range from 10 μm to 1500 μm or from 10 μm to 1000 μm or from 10 μm to 500 μm), and a second distribution wherein the particle size range of the second distribution comprises a particle size distribution that has a larger average, mean or mode than the average, mean or mode of distribution A. The average, mean or mode of distribution A is herein "M". In one embodiment the second distribution (or distribution B and/or C) has an average, mean, or mode distribution that is at least 1.1M, 1.5M, 1.75M, 2.0M, 2.5M, 3.0M, 3.5M, or from 1.1M to 4.5M, or 1.3M to 3.5M, or 1.4M to 2.5M or 1.5M to 2.0M.

In another embodiment the multimodal particle size distribution of the biodegradable abrasive particles comprises at least distribution A and distribution B wherein distribution A may comprise a particle size range from 10 μm to 300 μm or 50 μm to 300 μm and distribution B may comprise a particle size range from 300 μm to 1500 μm; and/or the biodegradable abrasive particles comprise at least distribution A, distribution B and distribution C, wherein distribution A may comprise a particle size range from about 10 μm to 300 μm or 50 μm to 300 μm, distribution B may comprise a particle size range from 300 μm to 600 μm and distribution C may comprise a particle size range from 600 μm to 1500 μm; and/or the biodegradable abrasive particles may comprise at least distribution A and distribution B wherein distribution A may comprise a particle size range from about 10 μm to 300 μm or 50 μm to 300 μm and distribution B may comprise a particle size range from 600 μm to 1500 μm.

In an embodiment the plurality of particles representing distribution B are visibly discernable.

The method of measuring the multimodal particle size distribution of the abrasive particles herein is described in the Test Methods section. The multimodal particle size distribution is measured using a Horiba LA-950 Particle Size Analyzer commercially available from Horiba International Corporation of Irvine, Calif.

In an embodiment the skin care composition comprises a higher weight % of biodegradable abrasive particles with distribution A than the second distribution wherein the second distribution comprises a particle size distribution that is larger (e.g. has larger average, mean or mode) than the particle size range of distribution A.

Also the skin care composition may comprise equal amounts of the biodegradable abrasive particles with distribution A, than the second distribution wherein the second distribution comprises a particle size distribution that is larger (e.g. has larger average, mean or mode) than the particle size range of distribution A.

Also distribution A may comprise from about 55% to about 90% by weight of the total abrasive particles and the second distribution (or distribution B) comprises from about 10% to about 45% by weight of the total abrasive particles.

Figure 1:
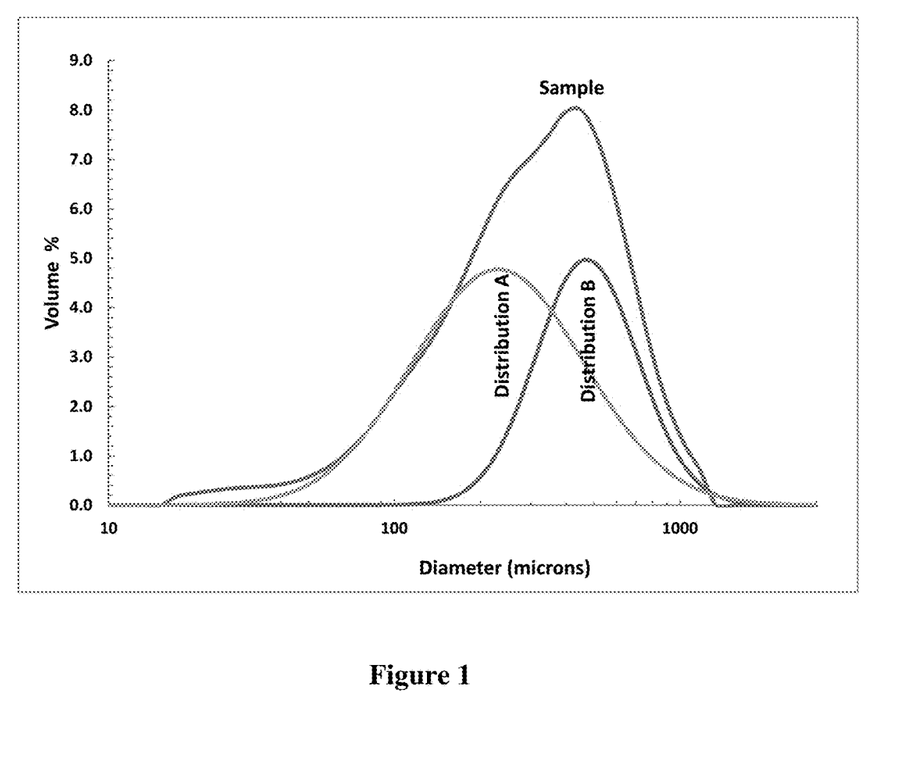
FIG. 1 shows a histogram of the particle size distribution curves showing a multimodal particle size distribution of a composition of the biodegradable abrasive particles of the present invention.
Figure 2:
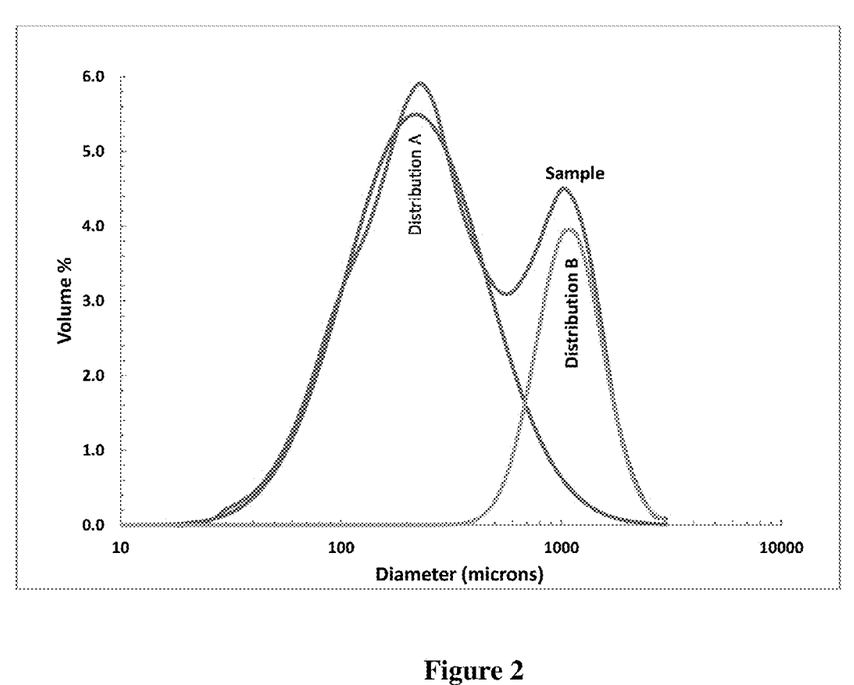
FIG. 2 shows a histogram of the particle size distribution curves showing a multimodal particle size distribution of an alternative composition of the biodegradable abrasive particles of the present invention.

FIGS. 1 and 2 show histograms of a multimodal particle size distribution of the biodegradable abrasive particles of the present invention. The x-axis of the histogram represents the ranges of the particle size. The vertical height or the y-axis represents the relative amount of particles or volume percent of that particle size, or the frequency of occurrences.

Tables 1 and 2 show and describe the multimodal particle size distribution for the histograms of FIGS. 1 and 2, respectively, listing parameters such as mean, average, mode, etc.

In Tables 1 and 2, D50 represents 50% of particles in the volume are less than the specified size. D10 represents 10% of particles in the volume are less than the specified size. D90 represents 90% of particles in the volume are less than the specified size. The mode is the value that occurs most often.

TABLE 1

| Statistics | Sample | Distribution A | Distribution B |
|---|---|---|---|
| D50 (μm) | 296.83 | 215.56 | 439.85 |
| D10 (μm) | 97.71 | 88.89 | 259.72 |
| D90 (μm) | 633.07 | 523.10 | 748.26 |
| Average (μm) | 337.09 | 273.68 | 478.85 |
| Mode (μm) | 419.90 | 214.10 | 423.75 |

TABLE 2

| Statistics | Sample | Distribution A | Distribution B |
|---|---|---|---|
| D50 (μm) | 278.65 | 204.88 | 1017.22 |
| D10 (μm) | 88.10 | 80.01 | 649.68 |
| D90 (μm) | 1145.62 | 523.46 | 1590.57 |
| Average (μm) | 472.15 | 267.50 | 1078.85 |
| Mode (μm) | 214.03 | 213.73 | 961.60 |

The skin cleansing compositions herein comprise biodegradable abrasive particles that may be selected or synthesized to possess irregular shapes such as non-spherical, non-rolling, and/or sharp or shaped particles and/or possess adequate hardness, to be effective for cleansing skin surfaces.

In an embodiment the biodegradable abrasive particles are non-rolling. Alternatively in another embodiment the biodegradable abrasive particles are preferably sharp. Non-rolling and/or sharp biodegradable abrasive particles provide good cleaning efficacy. The biodegradable abrasive particles herein may be non-spherical. By "non spherical" it is meant herein, having a shape different from a sphere and/or having a Form Factor (FF) of below 0.75. Preferably, the abrasive cleaning particles herein have a Form Factor (FT) of below 0.6, most preferably below 0.50 and/or from 0.1 to 0.75 and/or from 0.15 to 0.7. By "Form Factor (FF)" it is meant herein a dimensional indicator that defines how a given particle is different from a regular form of a sphere, based on the perimeter (p) of the particle outline, especially emphasizing irregular surface topology (e.g., surface roughness) as defined by ASTM F1877-05 (June 2009) chapter 11.3.6, wherein: $4*\pi*$Surface Area/Perimeter of Particle Outline$^2$ with "Surface Area" meaning the surface area of a particle and "Perimeter" being the outer contour of the particle.

In an embodiment shearing or graining methods described in the art to provide the biodegradable abrasive particles featuring irregular shapes and particle sizes defined by the targeted distribution range, may be employed. For example, grinding or milling the material may be accomplished by using jaw Crushers mills; rotor mills; cutting or blade or knife mills, impact or rotor and/or disc mills suchs as those manufactured by Retschz (see http://www.retsch.com/products/milling). In an embodiment the temperature is kept constant during the griding operation, whereas for example, suitable grinding temperature should not exceed 60° C. In an embodiment the grinding temperature is below 30° C., and/or may be below 0° C.

In an embodiment grinding may be achieved in cryogenic conditions using refrigerant media such as $CO_2$ or nitrogen in liquid conditions. Thus in another embodiment the milling is cryogenic milling with either ice or liquid nitrogen. Cryogenic milling is known in the art, see for example U.S. Pat. No. 6,699,963, Noda et al, issued Mar. 2, 2004, In one embodiment the sample of the PHA material is frozen and the PHA is then milled with a cryogenic mill to form the abrasive particles.

Other suitable means include the use of eroding tools such as a high speed eroding wheel with dust collector wherein the surface of the wheel is engraved with a pattern or is coated with abrasive sandpaper to promote to formation of the biodegradable abrasive particles herein.

In an embodiment, the biodegradable abrasive cleaning particles herein are single particles (e.g. are not aggregated or agglomerated particles).

Previous shaping processes are sometimes facilitated by mixing previous biodegradable abrasive materials as fillers within a thermoplastic or solidifying matrix of the biodegradable polymeric material.

Biodegradable abrasive particles may be sieved or otherwise separated and isolated to provide biodegradable abrasive particles with size ranges according to the multimodal size distributions herein. For example, selection of sieves with particular sizes may provide isolation of abrasive particles comprising at least distribution A and other sieves with other sizes to provide isolation of a second distribution such as distribution B wherein distribution A may comprise a particle size range from about 10 μm to 300 μm and distribution B may comprise a particle size range from 300 μm to 1500 μm. In other embodiments the a selection of sieves with particular sizes may be used to provide isolation of abrasive particle comprising narrower distribution of sizes such as from 50 μm to 300 μm falling within distribution A of 10 μm to 300 μm.

In addition, selection of sieves with particular sizes may provide isolation of abrasive particles comprising at least distribution A, and selection of different sieves sizes (v. the sieves sizes used for distribution A) to provide isolation of abrasive particles comprising a second distribution such as distribution B and/or distribution C. Then the particles of distribution A are combined with particles of the second distribution, and thereafter the combination is added to the skin care composition. Alternatively, the particles of distribution A and particles of the second distribution, may each be added separately to the skin care composition.

In another embodiment the milling step to generate the abrasive particles comprises the steps of: milling a first composition of biodegradable polymeric material or pellets to obtain abrasive particles with a particle size range of distribution A; milling a second composition of biodegradable polymeric material or pellets to obtain abrasive particles with a particle size range of the second distribution (e.g. distribution B and/or C); and mixing the first composition of abrasive particles with the second composition of abrasive particles to obtain a primary abrasive particle composition; and adding the primary abrasive particle composition into the skin cleansing composition. Alternatively, the particles of distribution A and particles of the second distribution (e.g. distribution B and/or C), may be added separately to the skin care composition.

In an embodiment the abrasive particles have size which may be defined by their area-equivalent diameter (ISO 9276-6:2008(E) section 7) also called Equivalent Circle Diameter ECD (ASTM F1877-05 Section 11.3.2). Mean ECD of particle population is calculated as the average of respective ECD of each particle of a particle population of at least 10 000 particles, preferably above 50,000 particles, more preferably above 100,000 particles after excluding from the measurement, and calculation the data of particles having area-equivalent diameter (ECD) of below 10 micrometers. Mean data are extracted from volume-based vs. number-based measurements.

Abrasive Particles Process Aids

Biodegradable abrasive particles may also contain process aids such as crystal nucleating agents, anti-oxidants, stabilizers, and rheology modifiers. In an embodiment the biodegradable polymer used to form the biodegradable abrasive particles may be blended with an amount of mineral, vegetable, soluble or insoluble fillers. Inclusion of a quantity of filler helps break the polymer into abrasive particles and features biodegradable particles with larger surface areas (e.g., via porosity and capillarity) which enhance the degradation kinetics. This is especially the case when the filler is water soluble. Typical fillers suitable for use with PHBV polymers include minerals (e.g., metal chlorides such as for example, NaCl, KCl, etc.; metal carbonates such as for example, $Na_2CO_3$, $NaHCO$, etc.; metal sulfates such as for example, $MgSO_4$). Generally all mineral adsorbents provide hardness, which is compatible with the overall target hardness of the biodegradable abrasive cleaning particle.

The filler can also be derived from vegetal feedstock, essentially from cellulose or lignocelluloses based material (e.g., nut shell, wood or bamboo fibers, corn cob, rice hull, etc. including carbohydrates such starch and flour, xanthan gum, alginic, dextran, agar, and the like). The suitable fillers may also be biodegradable and thus maintain the biodegradability of the final abrasive particles.

The biodegradable polymeric material that forms the particles such as PHBV polymers/particles, may comprise filler from about 1 wt % to 70 wt %, preferably from 2 wt % to 60 wt %, or more preferably from 5 wt % to 25 wt %, wherein wt % is relative to the total weight of the polymer/particles.

Hardness

The biodegradable abrasive particles herein, especially the particles comprising distribution A, should be hard enough to provide good cleaning/exfoliation performance while providing good surface safety and/or skin feel acceptability.

The hardness of the biodegradable abrasive particles in the present invention is determined as Vickers hardness which is measured according to standard ASTM E2546-07 and as noted in the Methods section herein.

The hardness of the biodegradable abrasive particles herein may be from 3 $kg/mm^2$ to 50 $kg/mm^2$, and/or from 5 $kg/mm^2$ to 35 $kg/mm^2$ and/or from 13 $kg/mm^2$ to 30 $kg/mm^2$, and/or 15 $kg/mm^2$ to 30 $kg/mm^2$ via the Vickers hardness method herein.

In an embodiment the particles are not significantly altered, e.g. do not degrade and break into smaller particles, during use of the composition herein.

Colorants

In one embodiment the plurality of biodegradable abrasive particles further comprises a colorant to provide a colored biodegradable abrasive particle. The biodegradable abrasive particles used in the present invention may be colored by the use of suitable dyes and pigments. The biodegradable abrasive particles herein may comprises a colorant which may be selected from the group consisting of organic pigments, inorganic pigments, interference pigments, lakes, natural colorants, pearlescent agents, dyes, and mixtures thereof. In an embodiment the pigments, lakes and/or dyes are hydrophobic. Other dyes and pigments are disclosed in *International Cosmetic Ingredient Dictionary and Handbook,* $10^{th}$ Edition, Volume 3, 2004, Colorants, pp. 2194-2197. In an embodiment the colorant comprises lakes such as Red Lake 40, Red Lake 7 and Yellow Lake 5.

In an embodiment the biodegradable abrasive particles comprise a safe and effective amount of a colorant, and/or from about 0.001% to about 5% by weight of the abrasive particles, of a colorant; in another embodiment from about 0.05% to about 3% by weight of the particles of a colorant.

A problem impacting colored abrasive particles is the bleeding or migration of color from the abrasive particles into the rest of the cleansing composition. This can be more problematic if the colored abrasive particles are used at higher concentrations or are used in opaque or white compositions.

Thus, in an embodiment the colored biodegradable abrasive particles are "color stable", As used herein "color stable" means that the colorant will not significantly bleed or migrate into the cleansing composition for the intended use and storage period.

In an embodiment the colored biodegradable abrasive particles comprise a homogeneous mixture of the colorant and the biodegradable polymeric material such as PHA. As used herein particles comprising a "homogeneous mixture" of the colorant and the biodegradable polymeric material means that the particles are formed by mixing the colorant and the biodegradable polymeric material so that the colorant is distributed, to some extent, throughout the biodegradable material and/or the interior of the particle. For example the colorant is not just applied to the surface of the biodegradable material. "Homogeneous mixture" also includes a uniform mixture of the colorant and the biodegradable polymeric material wherein the colorant is uniformly distributed throughout the biodegradable polymeric material and/or throughout the interior of the particle.

Figure 3:
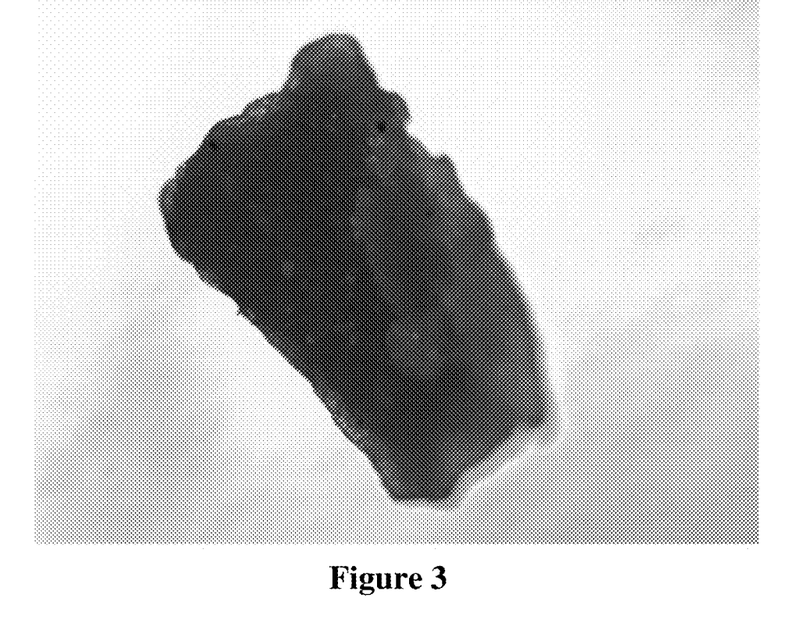
FIG. 3 is a photograph of the exterior of a particle having a homogeneous mixture of a colorant and a biodegradable polymeric material.
Figure 3A:
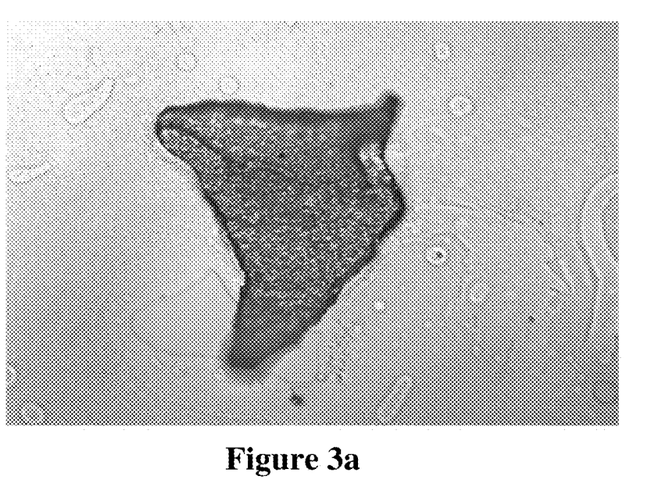
FIG. 3a is a photograph of the interior cross section of the particle of FIG. 3 having a homogeneous mixture of the colorant and a biodegradable polymeric material.
Figure 3B:
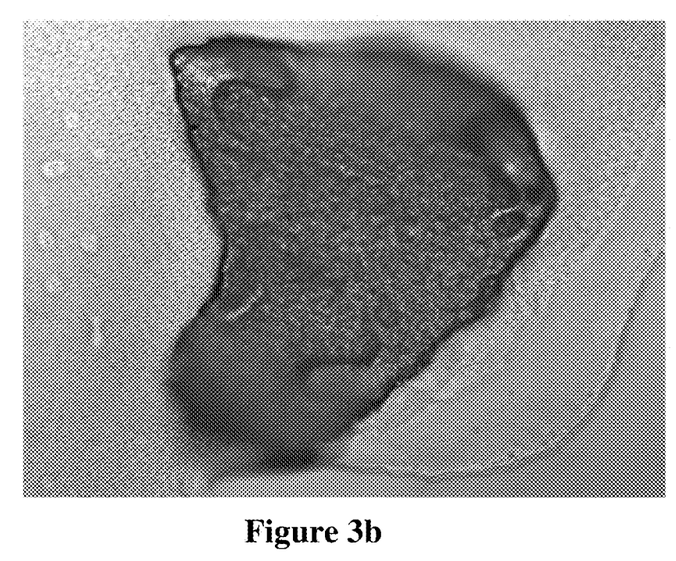
FIG. 3b is a photograph of an alternative interior cross section of the particle of FIG. 3 having a homogeneous mixture of the colorant and a biodegradable polymeric material.
Figure 3C:
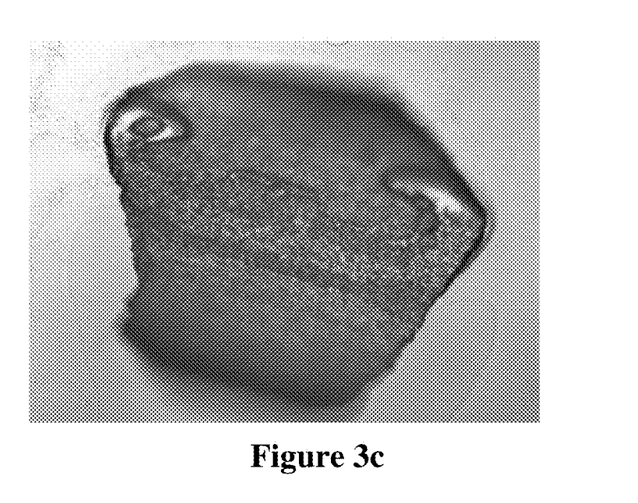
FIG. 3c is a photograph of an alternative interior cross section of the particle of FIG. 3 having a homogeneous mixture of the colorant and a biodegradable polymeric material.

An example of a particle having a homogeneous mixture of the colorant and a PHA biodegradable polymeric material is shown in FIG. 3. FIG. 3 is a photograph of the exterior of a particle having a homogeneous mixture of a colorant and a biodegradable polymeric material. The particle of FIG. 3 is made by adding and mixing the dye/colorant into the molten biodegradable polymeric material during extrusion and formation of the particles. FIG. 3a shows a interior cross-section view of the particle of FIG. 3. FIGS. 3b and 3c are photographs of alternative interior cross sections of the particle of FIG. 3.

Each image of FIGS. 3a, 3b and 3c consists of a 10 micron thick slice which was obtained using a Microtome: Thermo Scientific HN525NX; Light Microscope: ZEISS AXIOKOP 2 Plus; Magnification: 10×. Each of slices shown in 3a, 3b and 3c are taken at approximately 100 micron intervals from the previous slice on the fresh surface of the particle after slicing off 100 microns. Thus as shown in these figures the particles comprise a homogeneous mixture of the colorant and the biodegradable polymeric material where the colorant is dispersed to some extent through the cross section of the particle and may be dispersed uniformly throughout the entire polymeric material matrix and/or the interior of the particle.

Figure 4:
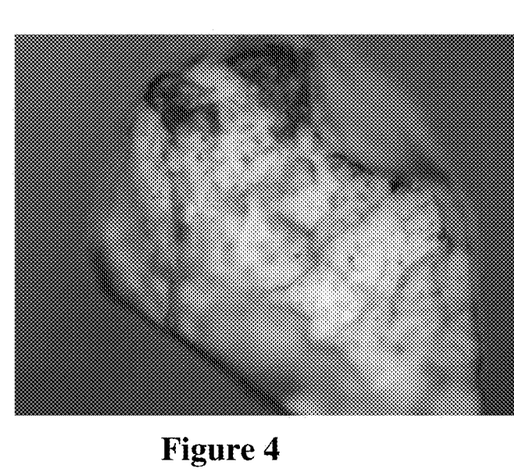
FIG. 4 is a photograph of the exterior of a particle having a non-homogeneous mixture of a colorant and a biodegradable polymeric material.
Figure 4A:
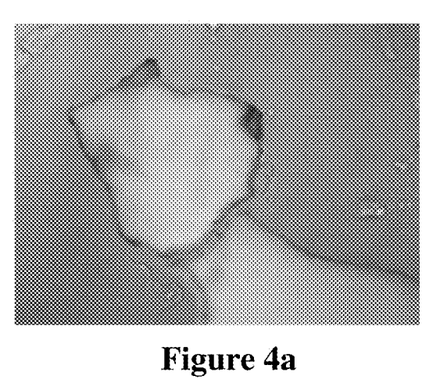
FIG. 4a is a photograph of an interior cross section of the particle of FIG. 4 having a non-homogeneous mixture of the colorant and a biodegradable polymeric material.
Figure 4B:
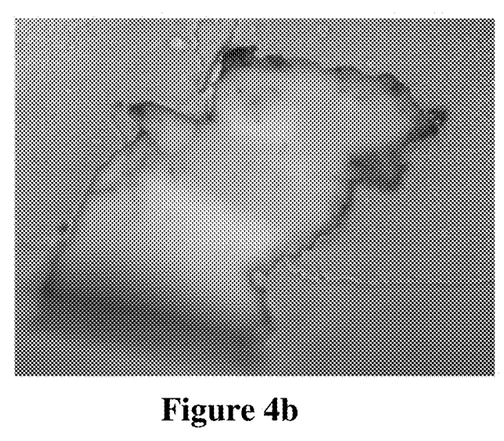
FIG. 4b is a photograph of an alternative interior cross section of the particle of FIG. 4 having a non-homogeneous mixture of the colorant and a biodegradable polymeric material.
Figure 4C:
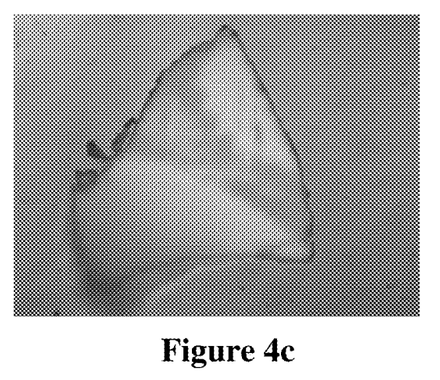
FIG. 4c is a photograph of an alternative interior cross section of the particle of FIG. 4 having a non-homogeneous mixture of the colorant and a biodegradable polymeric material.

An example of a particle having a non-homogeneous mixture of the colorant and a PHA biodegradable polymeric material is shown in FIG. 4. FIG. 4 shows a photograph of the exterior of an abrasive particle made by soaking the particle in a dye solution. FIG. 4a shows a cross-section view of the particle of FIG. 4. FIGS. 4b and 4c are photographs of alternative interior cross sections of the particle of FIG. 4 having a non-homogeneous mixture of the colorant and a biodegradable polymeric material. FIGS. 4a, 4b and 4c consist of a 10 micron thick slice of the particle which was obtained using a Microtome: Thermo Scientific HN525NX; Light Microscope: ZEISS AXIOKOP 2 Plus; Magnification: 10×. Each of slices shown in FIGS. 4a, 4b and 4c are taken at approximately 100 micron intervals from the previous slice on the fresh surface of the particle after slicing off 100 microns. As is observed these colored abrasive particles do not have a homogeneous mixture of the colorant and the biodegradable polymeric material through the interior of the particle. The color distribution is non-homogeneous on both the surface of the particle and in the interior of the particle. No significant amount of dye penetration is observed on the inside of the particle in FIGS. 4a, 4b and 4c.

In one embodiment a process of providing colored biodegradable abrasive particles with reduced colorant migration, for skin cleansing compositions, comprises the steps of:
(i) melting and extruding a sample of biodegradable polymeric material (e.g. PHA material such as PHBV);
(ii) optionally adding a sufficient amount of processing during the extrusion of the melted biodegradable polymeric material;
(iii) adding a colorant to the melted biodegradable polymeric material during extrusion and after the addition of the optional processing aid/filler whereby the colorant is mixed (e.g. homogeneously mixed) into the biodegradable polymeric material to form a mixture;
(iv) resolidifying (e.g. cooling) the extruded mixture of the biodegradable polymeric material comprising the colorant;
(v) processing (e.g. milling) the solidified mixture to generate biodegradable abrasive particles;
(vi) sieving the abrasive particles.

Thereafter, from about 0.5% % to about 15% by weight of the composition, of abrasive particles may be added into a skin cleansing composition to obtain a multimodal particle size distribution of the biodegradable abrasive particles.

PH

In another embodiment, the skin cleansing compositions herein are neutral compositions. In other preferred embodiments, the skin cleansing compositions herein have a pH in the range of from about 5.0 to about 6.0, more preferably from about 5.5 to about 7.5, wherein the pH is measured at 25° C.

Accordingly, the skin cleansing compositions herein may comprise suitable bases and acids to adjust the pH. A suitable base to be used herein is an organic and/or inorganic base. Suitable bases for use herein are the caustic alkalis, such as sodium hydroxide, potassium hydroxide and/or lithium hydroxide, and/or the alkali metal oxides such, as sodium and/or potassium oxide or mixtures thereof. A preferred base is a caustic alkali, more preferably sodium hydroxide and/or potassium hydroxide.

Other suitable bases include ammonia, ammonium carbonate, all available carbonate salts such as $K_2CO_3$, $Na_2CO_3$, $CaCO_3$, $MgCO_3$, etc., alkanolamines (e.g., monoethanolamine), urea and urea derivatives, polyamine, etc. Typical levels of such bases, when present, are from about 0.01 wt % to about 5.0 wt %, preferably from about 0.05 wt % to about 3.0 wt %, and more preferably from about 0.1 wt % to about 0.6 wt %, wherein the wt % is relative to the total weight of the composition.

The skin cleansing compositions herein may comprise an acid to trim its pH to the required level. Despite the presence of an acid, if any, the skin cleansing compositions herein will maintain their preferred neutral, pH as described herein above. A suitable acid for use herein is an organic and/or an inorganic acid. A preferred organic acid for use herein has a pKa of less than 6. A suitable organic acid is selected from the group consisting of citric acid, lactic acid, glycolic acid, succinic acid, glutaric acid and adipic acid and mixtures thereof. A mixture of the acids may be commercially available from BASF under the trade name Sokalan® DCS. A suitable inorganic acid is selected from the group consisting hydrochloric acid, sulfuric acid, phosphoric acid and mixtures thereof. A typical level of such an acid, when present, is from about 0.01 wt % to about 5.0 wt %, preferably from about 0.04 wt % to about 3.0 wt % and more preferably from about 0.05 wt % to about 1.5 wt %, wherein the wt % is relative to the total weight of the composition.

Carrier

The skin cleansing composition may comprise a dermatologically acceptable carrier. Dermatologically acceptable carriers may be selected for various stability, aesthetics, and/or compatibility with other materials present in the skin cleansing composition. Suitable carriers include water and/or water soluble solvents. The skin cleansing composition may comprise from about 1% to about 95% by weight of water and/or water equivalent solvent. The composition may comprise from about 1%, 3%, 5%, 10%, 15%, 20%, 25%, 30%, 35%, 40%, 45%, 50%, 55%, 60%, 65%, 70%, 75%, 80%, 85%, or 90% to about 90%, 85%, 80%, 75%, 70%, 65%, 60%, 55%, 50%, 45%, 40%, 35%, 30%, 25%, 20%, 15%, 10%, or 5% water and/or a water-equivalent solvent. "Water-equivalent solvent" refers to a compound which has a similar ability as water to solubilize a material. Suitable water-equivalent solvents include monohydric alcohols, dihydric alcohols, polyhydric alcohols, glycerol, glycols, polyalkylene glycols such as polyethylene glycol, and mixtures thereof. Particularly suitable solvents include lower aliphatic alcohols such as ethanol, propanol, butanol, isopropanol; diols such as 1,2-propanediol, 1,3-propanediol, butanediol, pentanediol, hexanediol, heptanediol, decanediol; glycerin; water, and mixtures thereof. In certain embodiments, the skin cleansing composition comprises water, diols, glycerin, and combinations thereof.

Suitable carriers also include oils. The skin cleansing composition may comprise from about 1% to about 95% by weight of one or more oils. Oils may be used to solubilize, disperse, or carry materials that are not suitable for water or water-equivalent solvents. Suitable oils include silicones, hydrocarbons, esters, fatty amides, ethers, and mixtures thereof. Oils may be fluid at room temperature. The oils may be volatile or nonvolatile. "Non-volatile" means a material that exhibits a vapor pressure of less than about 0.2 mm Hg at 25° C. at one atmosphere and/or a material that has a boiling point at one atmosphere of at least about 300° C. "Volatile" means that the material exhibits a vapor pressure of at least about 0.2 mm Hg at 20° C. Volatile oils may be used to provide a lighter feel when a heavy, greasy film is undesirable.

Suitable oils include volatile oils. In certain embodiments, the volatile oils may have a viscosity ranging from about 0.5 to about 5 centistokes 25° C. Volatile oils may be used to promote more rapid drying of the skin cleansing composition after it is applied to skin. Non-volatile oils are also suitable for use in the composition. Non-volatile oils are often used for emolliency and protective properties. Non-volatile oils preferably may have a viscosity ranging from about 5 to about 800,000 centistokes (or greater) or from about 20 to about 200,000 centistokes. Suitable examples of oils for use in the skin cleansing composition of the present invention are found in U.S. 2013/039961 (P&G).

Structuring Agent

The skin cleansing composition may comprise a structuring agent. Structuring agents may be used to increase viscosity, thicken, solidify, or provide solid or crystalline structure to the skin cleansing composition. The structuring agent may be used to suspend or disperse the abrasive particles. Structuring agents are typically grouped based on solubility, dispersibility, or phase compatibility. Examples of aqueous or water structuring agents include polymeric agents, natural or synthetic gums, polysaccharides, and the like. In one embodiment, the composition may comprises from about 0.0001%, 0.001%, 0.01%, 0.05%, 0.1%, 0.5%, 1%, 2%, 3%, 5% to about 25%, 20%, 10%, 7%, 5%, 4%, or 2%, by weight of the composition, of one or more structuring agents. Suitable examples of structuring agents for use in the skin cleansing composition of the present invention are found in U.S. 2013/039961 (P&G).

Optional Skin Cleansing Composition Ingredients

The skin cleansing composition may comprise one or more optional components to provide an efficacious and/or consumer desirable product. For example, the composition can include other actives or agents. For instance, suitable optional actives and agents may include an active or agent selected from a group consisting of sugar amines, vitamins, oil control agents, photosterols, hexamidine compounds, tightening agents, anti-wrinkle actives, anti-atrophy actives, flavonoids, N-acyl amino acid compounds, retinoids, peptides, UV actives, photostabilizers, anti-cellulite agents, desquamation actives, anti-acne actives, anti-oxidants, radical scavengers, conditioning agents, anti-inflammatory agents, tanning actives, skin lightening agents, antiperspirant actives, sensates, anti-dandruff actives, anti-melanogenic agent, sebum secretion inhibitors, blood circulating facilitating agent, softeners, keratine protecting agents, emollients, moisturizers, and combinations thereof.

Method of Using the Skin Cleansing Compositions

The present invention encompasses a method for cleansing a human's skin surface comprising topically contacting the skin surface with a skin cleansing composition according to the present invention and additionally followed by a rinsing step. Suitable skin surfaces herein include body, hands, and facial skin surfaces.

The use of biodegradable abrasive particles in the skin cleansing composition of the present invention is provided for delivering a benefit to skin surfaces selected from the group consisting of mild skin exfoliation, dirt removal from the skin surfaces and combinations thereof.

In a preferred embodiment, the composition according to the present invention is topically applied to the facial skin surface. "Facial skin surface" refers to one or more of the forehead, periorbital, cheek, perioral, chin, and nose skin surfaces.

The composition herein may be in its neat form or in its diluted form. By "in its neat form", it is to be understood that the composition is applied directly onto the skin surface to be treated without undergoing any dilution. By "diluted form", it is meant herein that the composition is diluted by the user typically with water. The composition is diluted prior to use to a typical dilution level of up to 10 times its weight of water. A usual recommended dilution level is 10% dilution of the composition in water.

The composition herein may be applied using the palms of the hands and/or fingers, or using an appropriate implement, such as a cloth, sponge, mask, razor, wand, cotton ball, swab, or pad, soaked in the diluted or neat composition herein. Furthermore, once applied onto the skin surface the composition may be agitated over the skin surface.

The method herein may optionally contain an additional rinsing step, preferably after the application of the composition. By "rinsing", it is meant herein contacting the surface cleaned/cleansed with the method according to the present invention with substantial quantities of appropriate solvent, typically water, directly after the step of applying the composition herein onto the skin surface. By "substantial quantities", it is meant herein between 0.001 L and 1 L of water per $m^2$ of skin surface, more preferably between 0.1 L and 1 L of water per $m^2$ of skin surface.

Test Methods

Hardness

The hardness of the biodegradable abrasive particles in the present invention is determined as Vickers hardness which is measured according to standard ASTM E2546-07. The Vickers hardness indentation measurement is carried out by using the Nano Hardness Tester (NHT), manufactured by CSM Instruments SA, Peseux, Switzerland, S/N 6-135 with module S/N 080820; software "indentation" version, for example 3.81.05. The NHT provides force and penetration depth measurements at nanometer length scales and has the following specifications:

Maximum displacement: 10 μm;
Displacement resolution: 0.3 nm;
Maximum force: 300 mN;
Force resolution; 5 μN.

The specimens used are powders and pellets, in a metallographic mount. Approximately 5-10 samples are measured and the hardness is recorded as $Kg/mm^2$ (Vickers). The indentation hardness ($H_{IT}$) is calculated by dividing the maximum force applied by the projected contact area at the maximum force. The following indentation parameters are used:

Maximum force (nM)—0.5, 1 and 5;
Loading time—1.5;
Unloading time—15;

Pause—10;
Adjust Depth Offset—150 000/15%;
Approach—1 500/10-25%;
Computation Method—Oliver & Pharr;
Poisson coefficient—0.50;
Indenter type—Berkovich Diamond (Indenter geometry-three sided pyramid; modified Berkovich α=65.3±0.3);
Indenter ID—B-J07;
Temperature—21-23 degrees C.
A value of 0.5 may be used to compute the modulus.

Biodegradability Test

The biodegradability of the abrasive particles can be tested according to the following method. This biodegradability test is based on the Organization for Economic Co-operation and Development (OECD) 301B $CO_2$ evolution biodegradation test method that screens chemicals for ready biodegradability in an aerobic aqueous medium.

In this test the test substance is suspended in a phosphate buffered media containing an activated sludge inoculums and the consumption of oxygen and/or the formation of carbon dioxide is measured via an electrolyctic respirometer. The test substance is the sole carbon and energy source and under aerobic conditions microorganisms metabolize organic substances producing $CO_2$ as the ultimate product. The test can run for 28 days or 90 days.

Particle Size Distribution Test Method

The particle size ranges of the abrasive particles herein are measured using a HORIBA LA-950 Particle Size Analyzer commercially available from Horiba International Corporation of Irvine, Calif.

The HORIBA LA-950 Particle Size Analyzer is set to operate in manual mode for the particle (e.g. PHBV particle) analyses. The main operational parameter settings are:

| | |
|---|---|
| Refractive index | 1.470-0.000i, (Water 1.333) |
| Circulation Speed | 6 (of 15) |
| Agitation Speed | 3 (of 15) |
| Ultra Sonic Power | 1 (of 7) |
| Ultra Sonic Time | Blank - 1 min, Sample - 3 min |

For each analysis the sample cup is filled with 200 mL of purified water, circulate, agitate and sonicate for one minute to remove bubbles from the system. Next, the laser is aligned and the blank sample is recorded prior to each analysis.

Each sample is prepared by gentle stirring with a spatula for a minute to alleviate any settling or agglomeration of aggregates. While the water in the sample cup is circulating and agitating, add enough sample (3 to 5 mL) using a transfer-tube to reduce the percent transmittance from 100 to 90+/−2%.

Once the baseline signal has stabilized to ensure the 90+/−2% transmittance, the sample is sonicated at power level 1 for 3 minutes before a measurement is taken. This process is repeated four times for each sample and the average of the analysis is reported.

Exemplary Skin Cleansing Compositions

| (w/w %) | Facial Cleanser - Synthetic Surfactant | | | Facial Cleanser - Cream | Facial Cleanser - Clear Gel | Thermal Scrub | Bar Soap |
|---|---|---|---|---|---|---|---|
| Water | qs | qs | qs | qs | qs | 0 | 12.000 |
| PEG-4 | | | | | | qs | |
| Disodium EDTA | 0.120 | 0.120 | 0.120 | 0.100 | 0.050 | | |
| Tetrasodium EDTA | | | | | | | 0.050 |
| PPG 15 Stearyl Ether | | | | 4.000 | | | |
| PPG-30 | | | | 0.250 | | | |
| Distearyldimonium Chloride | | | | 1.500 | | 0.8 | |
| Salicylic Acid | | | 2.000 | 1.800 | | | |
| Lauric Acid | 0.150 | | | | 2.000 | | |
| Sodium Tallowate | | | | | | | 68.080 |
| Magnesium Sulfate | | | | | | 20.000 | |
| Behentrimonium Chloride, Stearyl Alcohol | | | | | | 1.780 | |
| Sodium Palm Kernelate | | | | | | | 17.020 |
| Myristic Acid | | | | | 6.000 | | |
| Cetyl Betaine[3] | | | | 6.667 | | | |
| Sodium Myristoyl Sarcosinate | 5-10.00 | 5-10% | 5-10% | | | | |
| Dioleoylethyl Hydroxyethylmonium Methosulfate | | | | | | 2.000 | |
| Glycol Distearate (and) Sodium Laureth Sulfate (and) Cocamide MEA (and) Laureth 10[4] | 2.000 | | | | | | |
| Sodium Lauroamphoacetate | 10-20% | 10-20% | 10-20% | | | | |
| Sodium Trideceth Sulfate | 4-10% | 4-10% | 4-10% | | | | |
| Lauramidopropyl Betain | | | | | 10.00-20.00 | | |
| Sodium Lauryl Sulfate | | | | 3.571 | | | |
| PEG/PPG-300/55 Copolymer | | | | | | 3.000 | |
| PEG-100 | 0.200 | 0.200 | 0.200 | | | | |
| PEG 7M | | | | | 0.100 | | |
| Glycerin | 2.000 | 2.000 | 2.000 | 3.000 | 8.000 | | |
| Sorbitol (70%) | 2.857 | 2.857 | 2.857 | | | | |
| Citric Acid | 0.625 | 0.500 | 0.133 | | | | |
| Triethanolamine | | | | | 7.500 | | |
| Sodium Chloride | | | | | | | 0.600 |
| Coconut Acid | | | | | | | 1.000 |
| Steareth-2 | | | | 0.250 | | | |
| Steareth-21 | | | | 0.500 | | | |
| Stearyl Alcohol | | | | 2.880 | | 1.3 | |

-continued

| (w/w %) | Facial Cleanser - Synthetic Surfactant | Facial Cleanser - Cream | Facial Cleanser - Clear Gel | Thermal Scrub | Bar Soap |
|---|---|---|---|---|---|
| Behenyl Alcohol | | | 0.320 | | |
| Cetyl Alcohol | | | 0.800 | 0.5 | |
| Polyquaternium-10 (JR400) | 0.125 | | | | |
| Titanium Dioxide | | | | | 0.250 |
| Propylparaben | | | | 0.1 | |
| Methylparaben | | | | 0.2 | |
| Kathon | 0.030 | | 0.030 | | |
| DMDM (70%) and IPBC | | 0.400 | | 0.400 | |
| PEG-120 Methyl Glucose Dioleate | | 0.500 | | | |
| PEG-200 Hydrogenated/PEG-7 Glyceryl Cocoate/Water (Antil 200) | 3.500 | | | | |
| Hydroxypropylcellulose | | | | 0.25 | |
| Hydroxyethylcellulose[5] | | | 1.000 | | |
| Acrylates Co-polymer[1] | 3.90-4.667 | 3.90-4.667 | 3.90-4.667 | | |
| Poly(oxy-1,2-ethanediyl), alpha-hydro-omega-hydroxy-, ether with methyl D-glucopyranoside (4:1), tri-(9Z)-9-octadecenoate[2] | | | 0.625 | | |
| BHT | 0.040 | 0.040 | | | |
| Fragrance | 0.300 | 0.250 | 0.300 | 0.200 | 0.200 | 0.150 | 1.000 |
| Biodegradable abrasive particles made from PHBV Y1000/Y1000P granules (Tianan Biologic Materials Co., Ningbo, China); PHBV extruded with titanium dioxide and appropriate dye to provide bead color/Micropowders, Inc. Tradenames for PHBV incorporated into cleansing product chassis' are: PCX-3151, PCX-3152, PCX-3153, PCX-3162, PCX-3163, PCX-3177, PCX-3157, PCX-3158, PCX-3176, PCX-3153, PCX-3154, PCX-3174, PCX-3148, PCX-3149, PCX-3150, PCX-3155, PCX-3156, PCX-3175, PCX-3145, PCX-3146, PCX-3147, PCX-3142, PCX-3143, PCX-3144 | 0.5% - 50-300μ - PCX-3148 & 0.5% - 300-600μ - PCX-3143 | 3.7% - 50-300μ PCX-3148 & 1% - 50-300μ PCX- & 0.3% 300-600μ - PCX-3156 | 6% - 50-300μ PCX-3151, PCX-3148, PCX-3155, PCX3145, PCX-3142, PCX-3157, PCX-3162, or PCX-3152 and 3% - 600-1300μ of PCX-3153, PCX3177, PCX-3176, PCX-3174, PCX-3150, PCX-3175, PCX-3147, or PCX-3144 | 2.75% 50-300μ (Any color) & 0.25% 300 600μ (Any color) | 3% 50-300μ (Any Color) and 5% 300-600μ (Any Color) and 600-1300μ (any color) or 2% 50-300μ (any color) and 6% 300-600μ (any color) | 1.75% - 50-300μ - White 0.25% - 300-600μ - Red | 5% - 50-300μ PCX-3151, PCX-3148, PCX-3155, PCX3145, PCX-3142, PCX-3157, PCX-3162, or PCX-3152 and 3% - 600-1300μ of PCX-3153, PCX3177, PCX-3176, PCX-3174, PCX-3150, PCX-3175, PCX-3147, or PCX-3144 |
| Making Instructions | Mix water, beads, surfactant. Heat to 75 C. When solution is homogenous, add remaining ingredients, except fragrance & preservative. Cool to 40 C., add fragrance & preservative. | Phase A: Add water soluble ingredients & beads. Heat to 65 C. Phase B: Add oil soluble ingredients. Heat to 75 C. Pour Phase B into Phase A. Cool to 45 C. & add fragrance and preservative. | Phase A: Add all other ingredients except fragrance & preservative. Add beads. Heat to 65 C. Phase B: Create fatty acid premix. Heat to 75 C. Pour Phase B into Phase A. Cool to 45 C. and add preservative & fragrance. | Add all ingredients except beads while heating to 95 C. Mix until homogenous. Add beads. | The bar soap can be prepared in a conventional manner where soap noodles are mixed in an amalgamator with the perfume, titanium dioxide, and beads. The amalgamated mixture can then be refined with conventional bar soap refining equipment such as a mill or refining plodder. The refined mixture can then be extruded and cut into billets via a standard vacuum plodder, and bar cutter. The resulting billets can then be stamped into the desired shape using a |

| (w/w %) | Facial Cleanser - Synthetic Surfactant | Facial Cleanser - Cream | Facial Cleanser - Clear Gel | Thermal Scrub | Bar Soap |
|---|---|---|---|---|---|
| | | | | | conventional soap press. |

[1]Carbopol Aqua SF-1 ® from Noveon ™
[2]Glucamate LT from Lubrizol ™
[3]Mackam CET from Rhodia ™
[4]Euperlan PK 810 AM from Cognis ™
[5]Natursol 250 HRR from Hercules Inc.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A skin cleansing composition comprising:
   from 0.1% to 15%, by weight of the composition, of a plurality of biodegradable abrasive particles comprising a safe and effective amount, by weight of the particles, of polyhydroxy alkanoate (PHA) biodegradable polymeric material and a particle size range from 10 μm to 1500 μm;
   a multimodal particle size distribution of the biodegradable abrasive particles comprising distribution A comprising a particle size range from 10 μm to 300 μm and distribution B comprising a particle size range from 600 μm to 1500 μm; and
   a dermatologically acceptable carrier.

2. The skin cleansing composition of claim 1, wherein distribution A comprises from 55% to 90% by weight of the abrasive particles and distribution B comprises from 10% to 45% by weight of the abrasive particles.

3. The skin cleansing composition of claim 1, wherein the multimodal particle size distribution comprises distribution A, distribution B, and distribution C, and wherein distribution A comprises a particle size range from 10 μm to 300 μm, distribution B comprises a particle size range from 300 to 600 μm, and distribution C comprises a particle size range from 600 μm to 1500 μm.

4. The skin cleansing composition of claim 1, further comprising a ratio of abrasive particles of distribution A to distribution B is from 0.9:0.1 to 0.1:0.9.

5. The skin cleansing composition of claim 1, wherein the plurality of particles representing distribution B are visibly discernable.

6. The skin cleansing composition of claim 1, wherein the abrasive particles further comprise a colorant, wherein the colorant is selected from the group consisting of organic pigments, inorganic pigments, interference pigments, lakes, natural colorants, pearlescent agents, dyes, and mixtures thereof.

7. The skin cleansing composition of claim 6, wherein the biodegradable abrasive particles comprise a homogeneous mixture of the biodegradable polymeric material and the colorant.

8. The skin cleansing composition of claim 7, wherein the homogeneous mixture further comprises from 0.01% to 10% by weight of the particles, of $TiO_2$.

9. The skin cleansing composition of claim 1, wherein the composition comprises from 0.3% to 10% by weight of the composition of the biodegradable abrasive particles.

10. The skin cleansing composition of claim 1, wherein the biodegradable abrasive particles have a Form Factor (FF) of below 0.75.

11. The skin cleansing composition of claim 1, wherein the PHA is selected from the group consisting of poly-3-hydroxybutyrate (PHB), poly-3-hydroxyhexanoate, poly-3-hydroxy-valerate, poly-3-hydroxy-butyrate-co-3-hydroxy-valerate (PHBV), poly-3-hydroxybutyrate-co-3-hydroxyhexanoate (PHBH), and blends thereof.

12. The skin cleansing composition of claim 11, wherein the PHA is poly-3-hydroxy-butyrate-co-3-hydroxyvalerate (PHBV).

13. The skin cleansing composition of claim 1, wherein said abrasive particles have a hardness of from 3 $kg/mm^2$ to 50 $kg/mm^2$.

14. The skin cleansing composition of claim 13, wherein said abrasive particles have a hardness of from 13 $kg/mm^2$ to 30 $kg/mm^2$.

15. The skin cleansing composition of claim 1, wherein said skin cleansing composition has a viscosity from 100 cps to 1,000,000 cps.

16. The skin cleansing composition of claim 15, wherein said skin cleansing composition has a viscosity from 1,000 cps to 300,000 cps.

17. The skin cleansing composition of claim 1, wherein the biodegradable abrasive particles further comprises a Biodegradable Rate of 80% to 100% determined after 28 days according to the Biodegradability Test.

18. The skin cleansing composition of claim 1, wherein the biodegradable abrasive particles further comprises a Biodegradable Rate of 100% determined after 90 days according to the Biodegradability Test.

19. The skin cleansing composition of claim 1, wherein the composition further comprises additional abrasive particles comprising polymeric materials selected from the group consisting of:
   (a) one or more homo-polymers or co-polymers selected from the group consisting of polylactic acid derivatives (PLA), polycaprolactone (PLC), poly(glycolic acid) (PGA), and blends thereof;
   (b) aliphatic or, aromatic co-polyesters, wherein said co-polyester is selected from co-polyester containing succinic, adipic, terepthalic diacids, propanediol, butanediol, pentanediol monomer or blends thereof;
   (c) starch, thermoplastic starch (TPS), or blends thereof;
   (d) thermoplastic cellulose (TPC) derivative selected from the group consisting of cellulose ester, cellulose ether, cellulose alkanoate and blends thereof, and
   (e) combinations of (a) to (d).

20. The skin cleansing composition of claim 1, wherein said skin cleansing composition further comprises one or more actives selected from the group consisting of sugar amines, vitamins, oil control agents, photosterols, hexamidine compounds, tightening agents, anti-wrinkle actives, anti-atrophy actives, flavonoids, N-acyl amino acid compounds, retinoids, peptides, UV actives, photostabilizers, anti-cellulite agents, desquamation actives, anti-acne actives, anti-oxidants, radical scavengers, conditioning agents, anti-inflammatory agents, tanning actives, skin lightening agents, antiperspirant actives, sensates, anti-dandruff actives, anti-melanogenic agent, sebum secretion inhibitors, blood circulating facilitating agent, softeners, keratine protecting agents, emollients, moisturizers, and combinations thereof.

21. The skin cleansing composition of claim 1, wherein said skin cleansing composition is selected from the group consisting of a facial cleanser, body wash, hand cleanser and body cleanser.

22. A method for cleansing human skin surfaces comprising contacting said skin surface with the skin cleansing composition of claim 1, wherein said skin cleansing composition is topically applied onto said skin surface, and additionally followed by a rinsing step.

23. The skin cleansing composition of claim 1, wherein the multimodal particle size distribution comprises distribution A and a second distribution, wherein the average distribution of A is M, and the second distribution has an average distribution that is 1.1M to 4.5M.

24. The skin cleansing composition of claim 23 wherein the second distribution has an average distribution of 1.3M to 3.5M.

25. The skin cleansing composition of claim 23 wherein the second distribution has an average distribution of 1.4M to 2.5M.

* * * * *